(12) United States Patent  
Scott et al.

(10) Patent No.: US 7,566,335 B1
(45) Date of Patent: Jul. 28, 2009

(54) METHOD AND APPARATUS FOR PATELLA RESECTION

(75) Inventors: James W Scott, Tifton, GA (US); Timothy J Blackwell, Warsaw, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 887 days.

(21) Appl. No.: 10/994,990

(22) Filed: Nov. 22, 2004

(51) Int. Cl.
*A61B 17/60* (2006.01)
*A61F 2/00* (2006.01)

(52) U.S. Cl. ........................................ 606/88
(58) Field of Classification Search ............... 606/87, 606/88, 120, 151, 157
See application file for complete search history.

(56) References Cited

U.S. PATENT DOCUMENTS

| | | | |
|---|---|---|---|
| 1,089,362 A | 3/1914 | Hannifin | |
| 3,964,738 A * | 6/1976 | Owen | 269/221 |
| 4,130,938 A | 12/1978 | Uhlmann | |
| 4,364,381 A * | 12/1982 | Sher et al. | 606/96 |
| 4,565,192 A | 1/1986 | Shapiro | |
| 4,633,862 A | 1/1987 | Petersen | |
| 4,706,660 A | 11/1987 | Petersen | |
| 5,108,401 A | 4/1992 | Insall et al. | |
| 5,147,365 A | 9/1992 | Whitlock et al. | |
| 5,542,947 A | 8/1996 | Treacy | |
| 5,667,512 A | 9/1997 | Johnson | |
| 5,716,362 A | 2/1998 | Treacy | |
| 5,944,723 A | 8/1999 | Colleran et al. | |
| 7,344,540 B2 * | 3/2008 | Smucker et al. | 606/87 |
| 2003/0163137 A1 | 8/2003 | Smucker et al. | |

* cited by examiner

*Primary Examiner*—Anu Ramana
(74) *Attorney, Agent, or Firm*—Harness, Dickey

(57) ABSTRACT

A medical device for holding a patella including a clamping assembly configured to hold the patella and an actuating assembly connected to the clamping assembly. The actuating assembly moving the clamping assembly from an open position to a closed position, wherein the actuating assembly is generally orthogonal to the clamping assembly. The medical device can hold the patella ninety degrees from its normal position to resect the patella.

20 Claims, 11 Drawing Sheets

METHOD AND APPARATUS FOR PATELLA RESECTION

FIELD

The present invention relates to a bone resection device and more particularly relates to a patella resection and positioning device with a clamping assembly that is orthogonal to an actuating assembly.

BACKGROUND

With reference to FIG. 1 and FIG. 2, a human knee joint is shown and generally indicated by reference numeral 10. The knee joint 10 is a junction of four bones: a femur 12, a tibia 14, a fibula 16 and a patella 18. Myriad medical problems can require partial or complete replacement of one or more portions of the aforesaid bones that form the knee joint 10. When using a prosthetic device to replace portions of the knee joint 10, positioning and preparation of the bones may be necessary to provide a proper fit for one or more prosthetic devices. Positioning and preparation of the patella can include, for example, exposing a posterior side 20 of the patella 18 to resect portions thereof in preparation for attachment of a patella prosthetic.

When implanting the prosthetic on the patella 18, access to the posterior side 20 requires an incision 22 in the skin 24 adjacent to the knee joint 10. A medical professional may aide in healing and recovery by reducing the number of incisions 22, reducing the respective size of each of the incisions 22 or reducing the magnitude of manipulation of the patella bone 18. On the other hand, the size of incisions 22 in minimally invasive procedures may limit the amount and size of the equipment that may be used in vivo or adjacent to the incision 22. Furthermore, any reductions in complexity and any increase in efficiency of the equipment may be realized in reductions in cost and procedure complexity and reductions in discomfort and recovery time.

SUMMARY

A medical device for holding a patella including a clamping assembly configured to hold the patella and an actuating assembly connected to the clamping assembly. The actuating assembly moving the clamping assembly from an open position to a closed position, wherein the actuating assembly is generally orthogonal to the clamping assembly.

Further areas of applicability of the present invention will become apparent from the detailed description provided hereinafter. It should be understood that the detailed description and specific examples, while indicating the various embodiments of the invention, are intended for purposes of illustration only and are not intended to limit the scope of the invention.

BRIEF DESCRIPTION OF THE DRAWINGS

The present invention will become more fully understood from the detailed description, the appended claims and the accompanying drawings, wherein:

DETAILED DESCRIPTION OF THE VARIOUS EMBODIMENTS

The following description of the various embodiments of the present invention is merely exemplary in nature and is in no way intended to limit the invention, its application or uses. While the illustrated embodiments pertain to one knee joint of the human body, it is appreciated that the present invention is applicable to various other bones of the human body including both knee joints. It is also appreciated that the present invention is applicable to bones of other animals, mammalian or otherwise, which may require prosthetic replacements due to various medical concerns.

Figure 4:
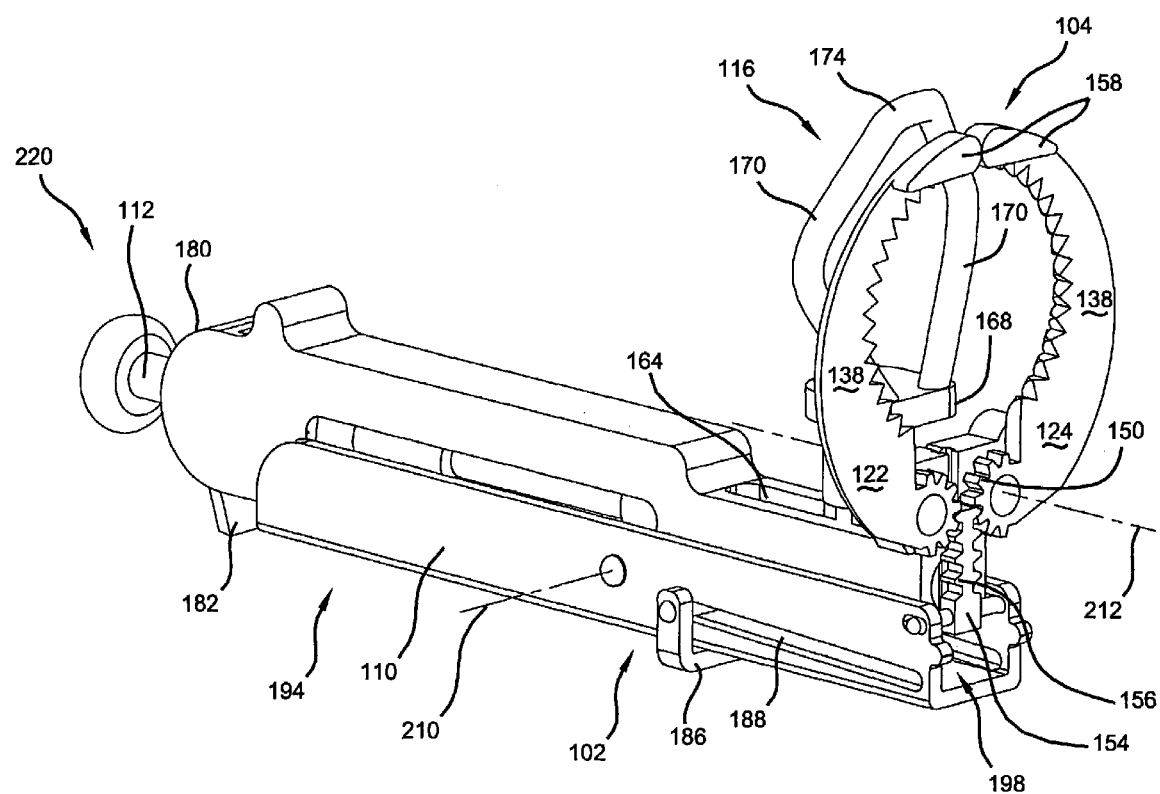
FIG. 4 is similar to FIG. 3 but shows the medical device in a closed position.
Figure 5:
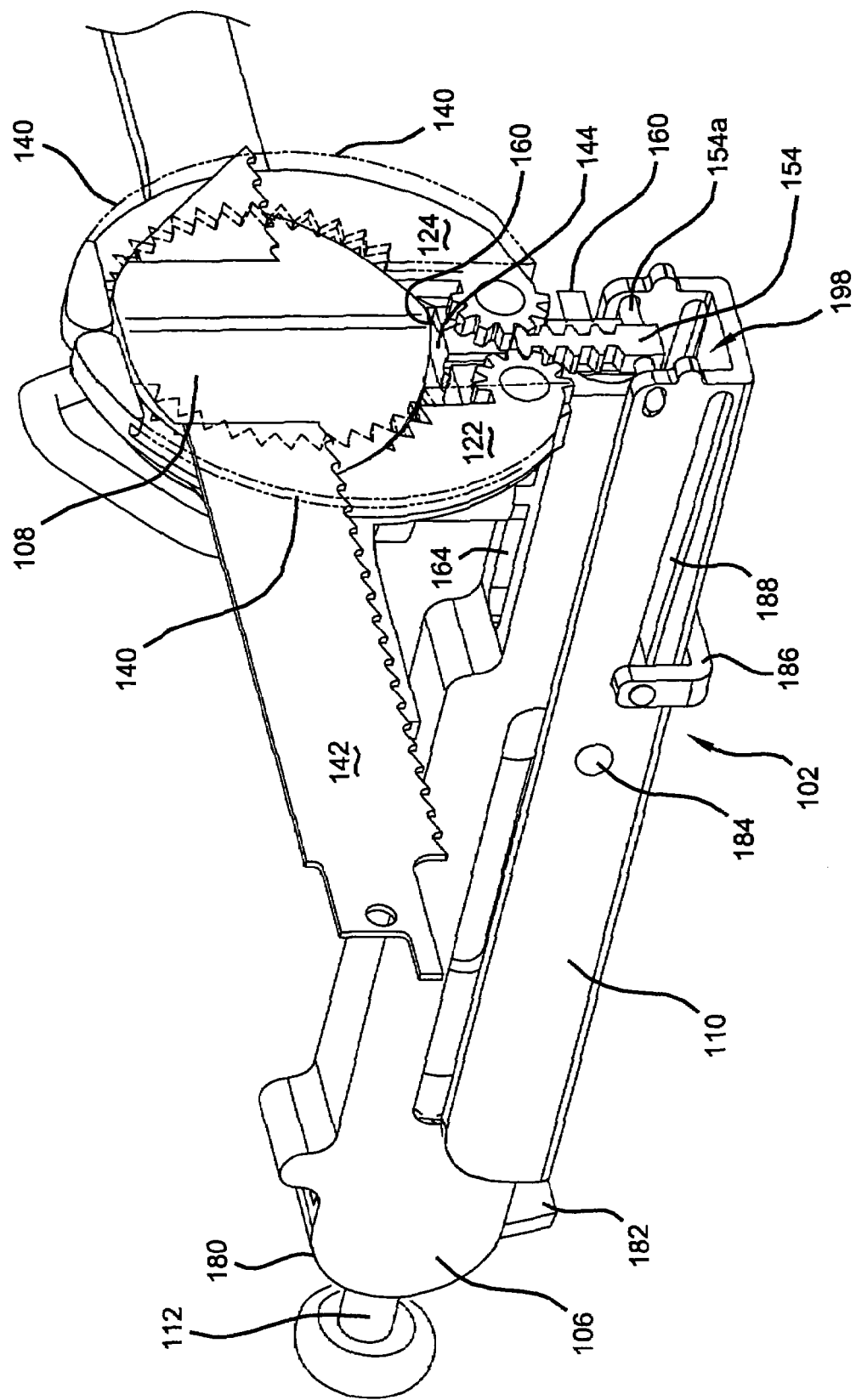
FIG. 5 is similar to FIG. 3 but shows another configuration of the clamping assembly with a cutting tool.

With reference to FIG. 3 through FIG. 11, a medical device for patella positioning and resection is generally indicated by reference numeral 100. The medical device 100 includes an actuating assembly 102 connected to a clamping assembly 104 both of which are connected to a handle member 106. The actuating assembly 102 opens and closes the clamping assembly 104 around, for example, a patella 108 (FIG. 5). The actuating assembly 102 includes a lever member 110 and a plunger member 112 both of which are connected to the clamping assembly 104. The clamping assembly 104 includes a posterior member 114 and an anterior member 116. The posterior member 114 can be configured to hold the patella 108 in vivo while the anterior member 116 clamps over an exterior surface 118 of the skin 120 to further hold the patella 108 within the clamping assembly 104, which is shown in greater detail in FIG. 9 through FIG. 11.

Figure 9:
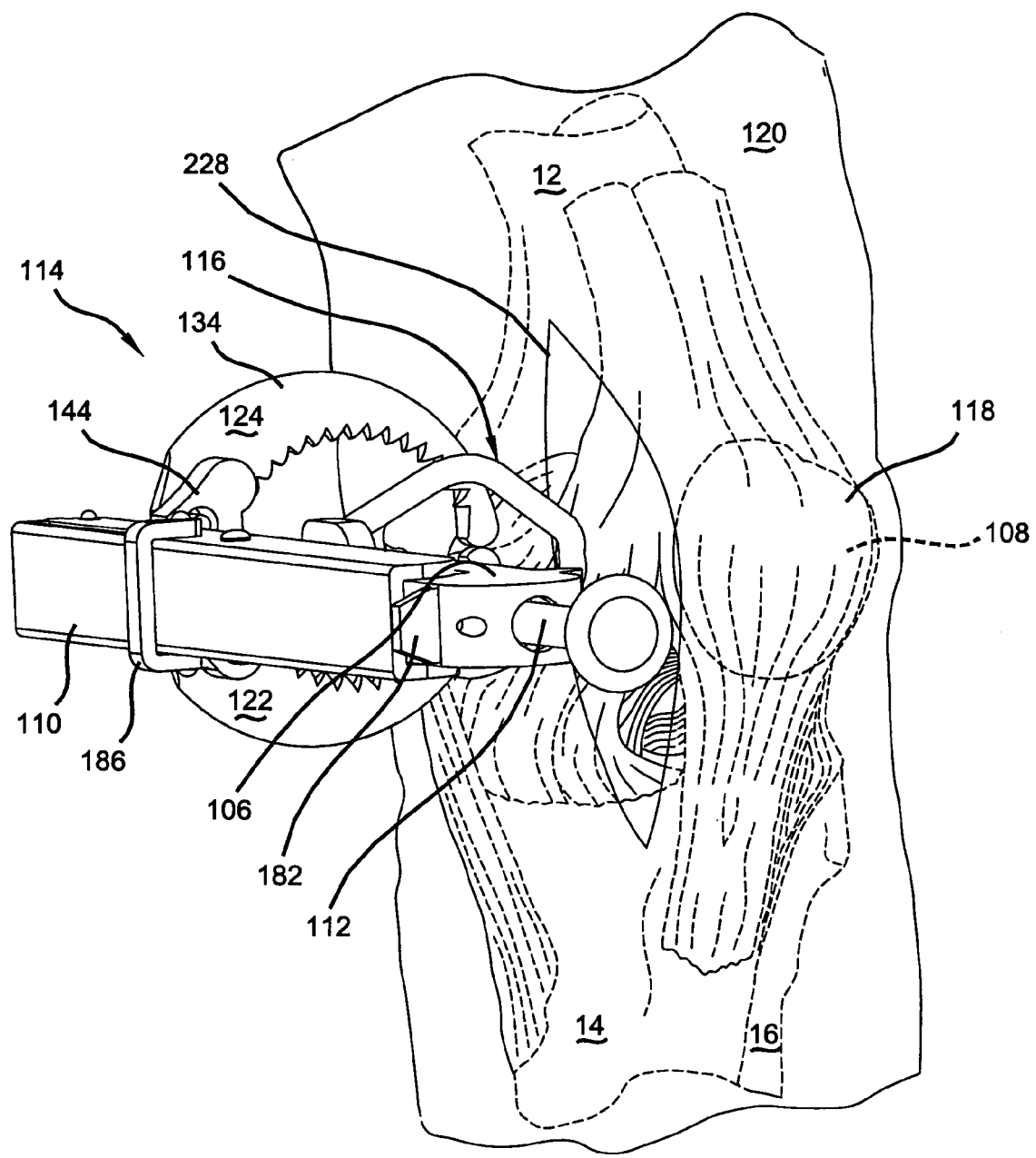
FIG. 9 is a perspective view of the medical device of FIG. 3 positioned outside of an incision in the skin surrounding the knee joint.

With reference to FIG. 3 through FIG. 6, the posterior member 114 of the clamping assembly 104 includes a first jaw 122 and a second jaw 124, which may be collectively referred to hereinafter as jaws 126. Each of the jaws 126 has an inboard face 128, and outboard face 130, a posterior face 132 and an anterior face 134 (FIG. 9). A plurality of teeth 136 is formed on the inboard face 128 to engage the patella 108. On the posterior face 132 of each jaw 126 is a reference portion 138 configured as a cutting index to, for example, resect portions of the patella 108. With specific reference to FIG. 5 and FIG. 6, a saw tooth slot 140 is formed in each of the jaws 126 and passes from the outboard face 130 through to the inboard face 128, such that a tool 142 can be passed therethrough and used to, for example, resect the patella. The tool 142 can include, for example, but are not limited to a saw, a reamer or a burr. It is appreciated that the cutting tool can abut portions of the cutting slot 140 or the reference portion 138 when resecting the patella 108.

Figure 6:
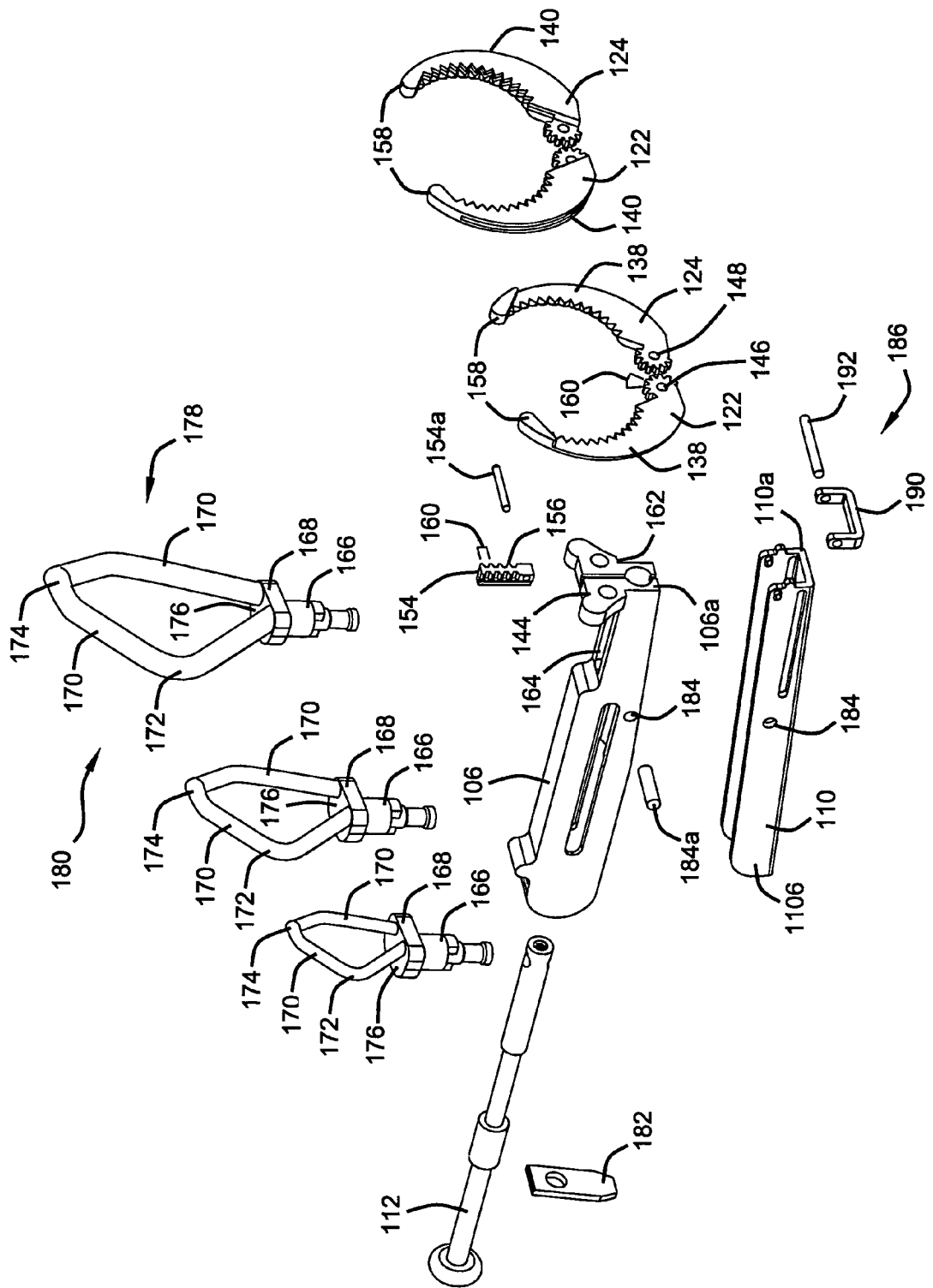
FIG. 6 is an exploded assembly view of the medical device of FIG. 3.

The first jaw 122 and the second jaw 124 are connected to a jaw bracket 144 at a first jaw connection point 146 and a second jaw connection point 148. The first jaw 122 pivots about the first jaw connection point 146 and the second jaw pivots 124 about the second jaw connection point 148. The first jaw 122 includes a first set of gear teeth 150 and the second jaw 124 also includes a second set of gear teeth 152, which can be similar to the first set of gear teeth 150. A rack 154 having gear teeth 156 meshes with the respective gear teeth 150, 152 of the first jaw 122 and the second jaw 124. The rack 154 slidingly engages the jaw bracket 144 and can connect to the handle member 110 with a rack pin 154a (FIG. 6). As the rack 154 moves in and out, the first jaw 122 and the second jaw 124 open and close, respectively.

More specifically, as the rack 154 is drawn away from tips 158 of the first jaw 122 and the second jaw 124, the jaws 126 close. As the rack 154 is pushed toward the tips 158 of the first jaw 122 and the second jaw 124, the jaws 126 open. It is appreciated that a tooth pitch 160 of the respective gears 150, 152 and 156 on the rack 154 and the first jaw 122 and the second jaw 124 can be configured to open and close the first jaw 122 and the second jaw 124 at a uniform rate. It is also appreciated that the tooth pitch 160 of the respective first jaw 122, the second jaw 124 and the rack 154 can be varied so that motion of the rack 154 can produce dissimilar opening and closing rates of either the first jaw 122 or the second jaw 124.

The jaw bracket 144 is attached to the handle member 106 with a jaw bracket flange 162. The jaw bracket flange 162 holds the clamping assembly 104 at an orientation perpendicular to the handle member 106 providing an overall L-shape to the medical device 100. In the various embodiments, the jaw bracket flange 162 connects the jaw bracket 144 to the handle member 106 at a distal end 106a of the handle member 106. Disposed above the jaw bracket 144 is an elongated groove 164 in which the anterior member 116 of the clamping assembly 104 travels.

The anterior member 116 of the clamping assembly 104 includes a post 166 that travels within the elongated groove 164 of the handle member 106. A backing member 168 is attached to the post 166, while a pair of arcuate rods 170 is attached to the backing member 168. The arcuate rods 170 are each generally V-shaped such that a point 172 of the V-shape is disposed in a direction opposite the posterior portion 114. One set of ends 174 of the V-shaped arcuate rods 170 are connected together, while opposite ends 176 are connected to and cantilevered off the backing member 168. Because each of the arcuate rods 170 have a V-shape and are opposed to one another, a concave surface 178 is formed. It follows that a convex surface 180 is formed opposite the concave surface 180. The concave surface 178 is orientated toward the distal end 106a where the jaw bracket flange 162 attaches to the handle member 106. When the anterior member 116 is directed toward the posterior member 114 of the clamping assembly 104, the concave surface 178 holds, for example, the patella 108 between the posterior member 114 and the anterior member 116 of the clamping assembly 104, as shown in FIG. 5.

The anterior member 116 is connected to the plunger member 112, which is contained within the handle member 106. More specifically, the post 166 connects the plunger member 112 to the backing member 168 such that the post 166 travels in the elongated groove 164. Pushing the plunger member 112 toward the distal end 106a of the handle member 106 moves the anterior member 116 of the clamping assembly 104 toward the posterior member 114. An anterior section 180 of the handle, in which the plunger member 112 is disposed, can be configured such that there is resistance in response to motion of the plunger member 112. The resistance can be configured so that when the plunger member 112 is pushed toward the jaws 126, the anterior member 116 remains in place. The plunger member 112 can be pulled back in a direction opposite the jaws 126, which pulls the anterior member 116 away from the posterior member 114.

A locking tab 182 can connect to the handle member 106 and can hold the plunger member 112. The locking tab 182 can be slightly deflected to unlock the plunger member 112 thus allowing unrestricted movement. It is appreciated that the above mentioned sliding resistance configuration can be substituted or combined with other suitable mechanisms to secure the anterior member 116 of the clamping assembly 104. Other such mechanisms include, for example, but are not limited to, a worm drive, a ratcheting mechanism or a powered drive system with an electric or pneumatic motor.

The lever member 110 of the actuating assembly 102 is connected to the handle member 106 at a lever member pivot point 184. The lever member 110 can be pivoted about the lever member pivot point 184 and the pivot pin 184a relative to the handle member 106. More specifically, the lever member 110 has a clamp end 110a distal from a free end 110b. The clamp end 110a is connected to the rack 154, which is connected to the sets of teeth 150, 152 on both the first jaw 122 and the second jaw 124. Squeezing the lever member 110 such that the free end 110b pivots and comes into contact with the handle member 106 causes the clamp end 110a to pivot away from the handle member 106 thus pulling the rack 154 away from the mounting bracket. Pulling the rack 154 away from the jaw bracket 144 causes the first jaw 122 and the second jaw 124 to close.

A slide 186 can be disposed in a pair of channels 188 on the clamp end 110a of the lever member 110. The slide 186 includes an U-shaped handle 190 and is connected to a rod 192 that is disposed through the U-shaped handle 190 and the channels 188. With the lever member 110 in a clamped position 194 (FIG. 4), such that the free end 110b is closer to the handle member relative to an open position 196 (FIG. 3), a space 198 opens up between the clamp end 110a of the lever member 110 and the handle member 106. The slide 186 can be pulled up through the channels 188 of the lever member 110 such that the rod 192 of the slide 186 can block the clamp end 110a of the lever member 110 from returning to the open position 196. As such, the slide 186 prevents rotation of the lever member 110 back to the open position 196. The channels 188 on the clamp end 110a of the lever member 110 may be configured in a taper lock configuration 200 that provides sliding resistance to the slide 186 as it is moved from an unlocked position 202 to a locked position 204. It is appreciated that in the locked position 204, the lever member 110 is in a partially or fully clamped position 194.

The lever member 110 is configured to pivot about the pivot point 184 such that when the first jaw 122 and the second jaw 124 are in an open position 206, the free end 110b of the lever member 110 can be approximately fifteen (15) degrees from the handle member 106. It is appreciated that when the lever member 110 is pivoted to close the first jaw 122 and the second jaw 124, the lever member 110 can rotate to a generally parallel position 208 relative to the handle member 106.

The lever member 110 and the handle member 106 are generally orthogonal to the clamping assembly 104. As such, an actuating assembly axis of rotation 210 upon which lever member 110 pivots is generally orthogonal to a clamping assembly axis of rotation 212 upon which the jaws 126 pivot to move from the open position 206 to a closed position 214 and a plurality of positions therebetween as shown in FIG. 4. It is also appreciated that an engaging direction 216 upon which the plunger member 112 travels to move the anterior member 116 of the clamping assembly 104 from an open position 218 (FIG. 3) to a closed position 220 (FIG. 4) is generally orthogonal to a plane defined by the jaws 126.

In the various embodiments of the present invention, the actuating assembly 102 can be configured as a worm drive, which may drive the jaws 126 from the open position 206 to the closed position 214. More specifically, a threaded rod may be used to engage the sets of teeth 150, 152 on the jaws 126 such that rotation of the threaded rod causes the first jaw 122 and the second jaw 124 to close at a uniform rate. It is appreciated that additional gearing may be installed between the worm drive and the sets of gear teeth 150, 152 on the jaws 126 to provide dissimilar opening and closing rates. Furthermore, gearing between the lever member 110 and the jaws 126 can further include a ratcheting mechanism to increase clamping force between jaws 126 or to otherwise index motion of either the first jaw 122 or the second jaw 124. In other embodiments of the present invention, the rack 154 may only have teeth on one side such that the rack 154 will only engage and thereby move one jaw when it is drawn from the open position 206 to the closed position 214. More specifically, a jaw can be fixed while the other jaw can be moved toward the fixed jaw due to the motion of the rack 154. It is also appreciated that an actuating force required to move the jaws 126 from an open position 206 to a closed position 214 and therebetween can be applied by mere rotation of the lever member 110 by a user or can be initiated by the user but performed by an electric motor or some other powered assistance device.

Figure 7:
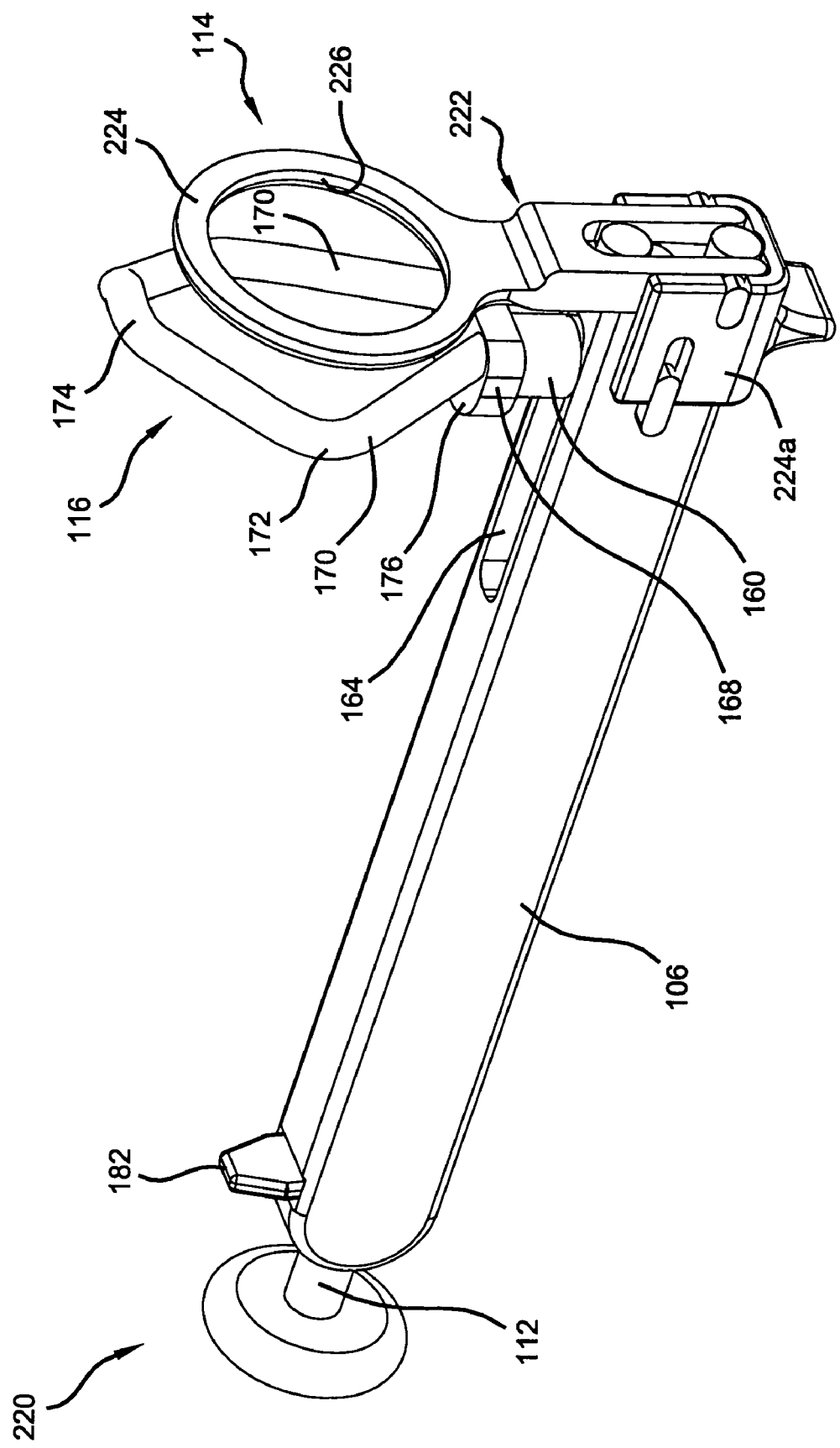
FIG. 7 is a perspective view of the medical device of the present invention showing a ring assembly constructed in accordance with the various embodiments of the present invention.
Figure 8:
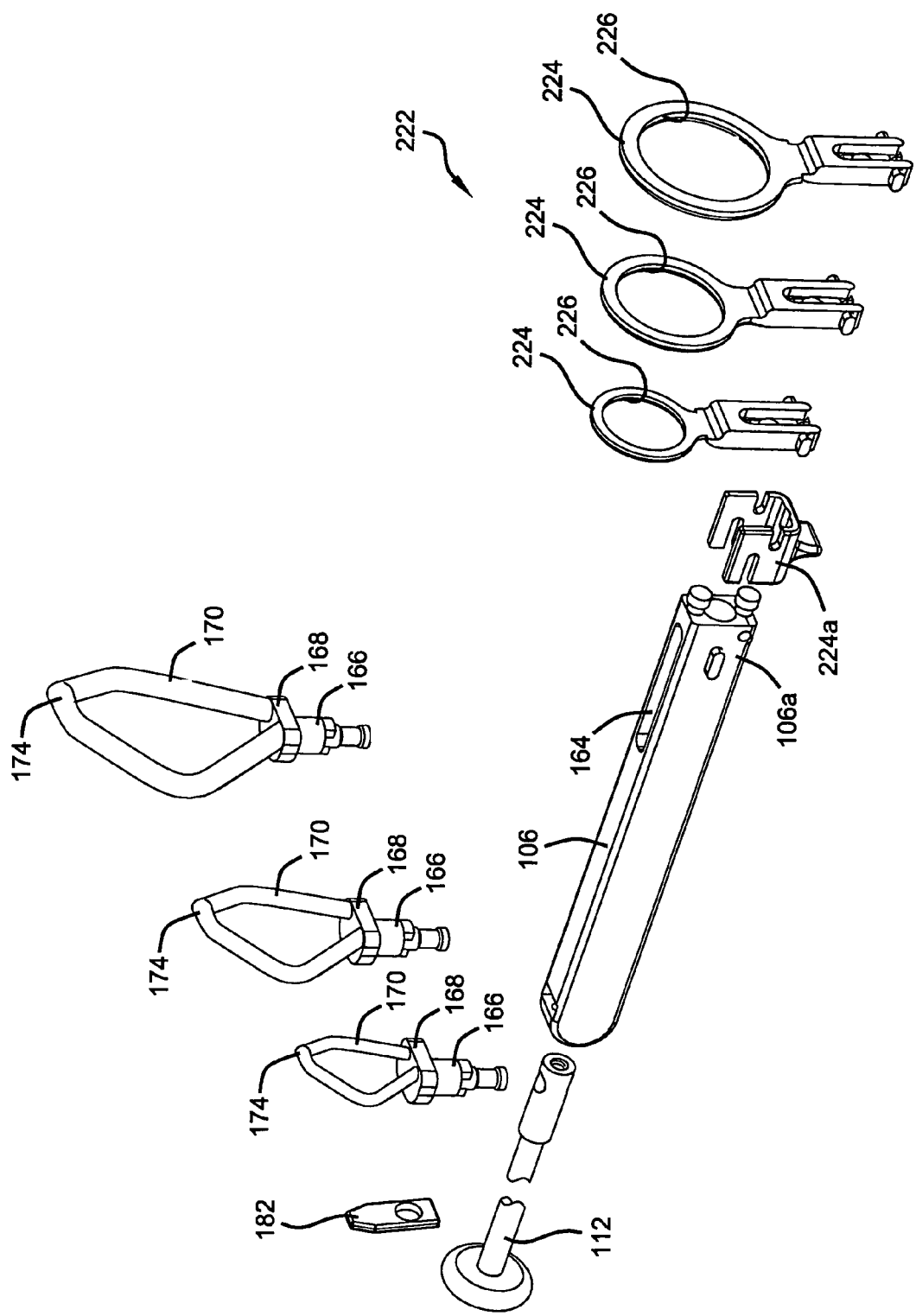
FIG. 8 is an exploded assembly view of the medical device of FIG. 7.

With reference to FIG. 7 and FIG. 8, the posterior member 114 of the clamping assembly 104 in the various embodiments of the present invention can also include a ring assembly 222 in lieu of the jaws 126. The ring assembly 222 can be attached to the distal end 106a of the handle member 106. In this exemplary arrangement, the anterior member 116 of the clamping assembly 104 in the closed position 220 presses, for example, the patella 108 between the ring assembly 222 and the anterior member 116 of the clamping assembly 104. It is appreciated that various sizes of the ring assembly 222 can be connected to the handle 14. More specifically, the user can measure, for example, the patella 108 and determine the proper diameter of a ring 224 on the ring assembly 222 such that the ring assembly 222 holds the patella 108 in the proper position. Different ring 224 sizes can be installed with the same ring assembly bracket 224a.

In the various embodiments of the present invention, the ring assembly 222 can hold the patella 108 thus making contact with bone or can hold various portions of the connective and muscle tissue. As discussed earlier, the jaws 126 are configured to engage at least a portion of the patella 108. In various embodiments of the present invention, the ring assembly 222 can be configured to only hold the connective tissue and the muscle tissue that surrounds the patella 108 but not make direct contact with the patella 108. It is appreciated that the ring assembly 222 can be configured such that the ring assembly 222 may make direct contact with the patella 108. Nevertheless, the ring assembly 222 can be configured such that proper positioning of the patella 108 is achieved by wedging the patella 108 against a side 226 of the ring assembly 222 during, for example, a resection process. More specifically, with the patella 108 held between the ring assembly 222 and the anterior member 116 of the clamping assembly 104, various resection processes will cause the patella 108 to wedge up against the clamping assembly 104 thereby holding the patella 108 securely.

In various embodiments of the present invention, the ring 224 can be configured such that portions of the ring 224 have a cylindrical shape. The cylindrical shape of the ring assembly 222 is configured to accept an associated circular reaming device that can be inserted into the cylindrical shape of the ring assembly 222. The circular reamer, for example, can include irrigation holes to facilitate washing away debris while reaming the patella 108. The circular reamer or other suitable tools can be driven by hand or be driven by an electrical machine or other suitable motor. The ring 224 can also have depth stops located to provide depth indication for the circular reamer.

Figure 10:
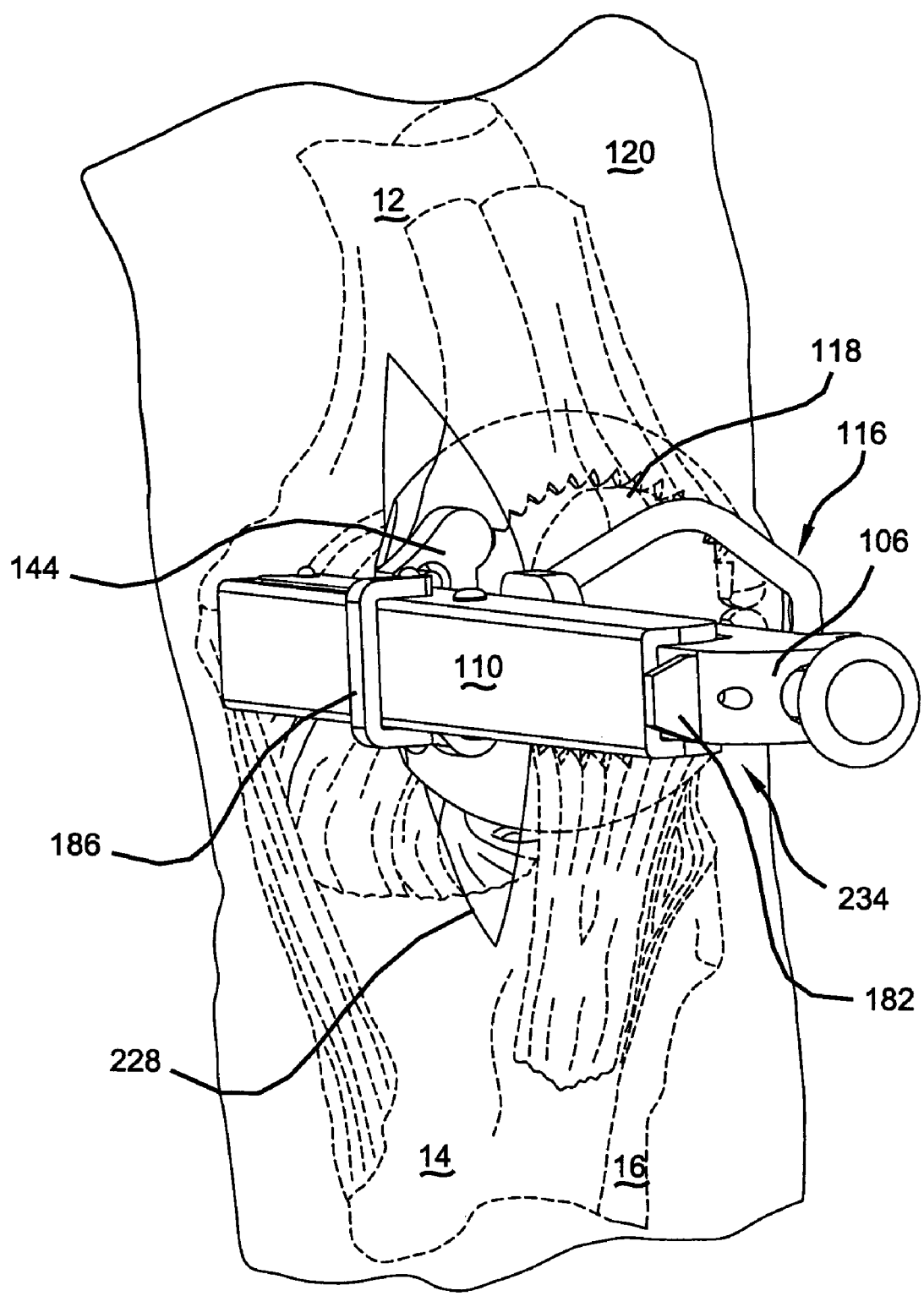
FIG. 10 is similar to FIG. 9 but shows the medical device placed in the incision and holding the patella.
Figure 11:
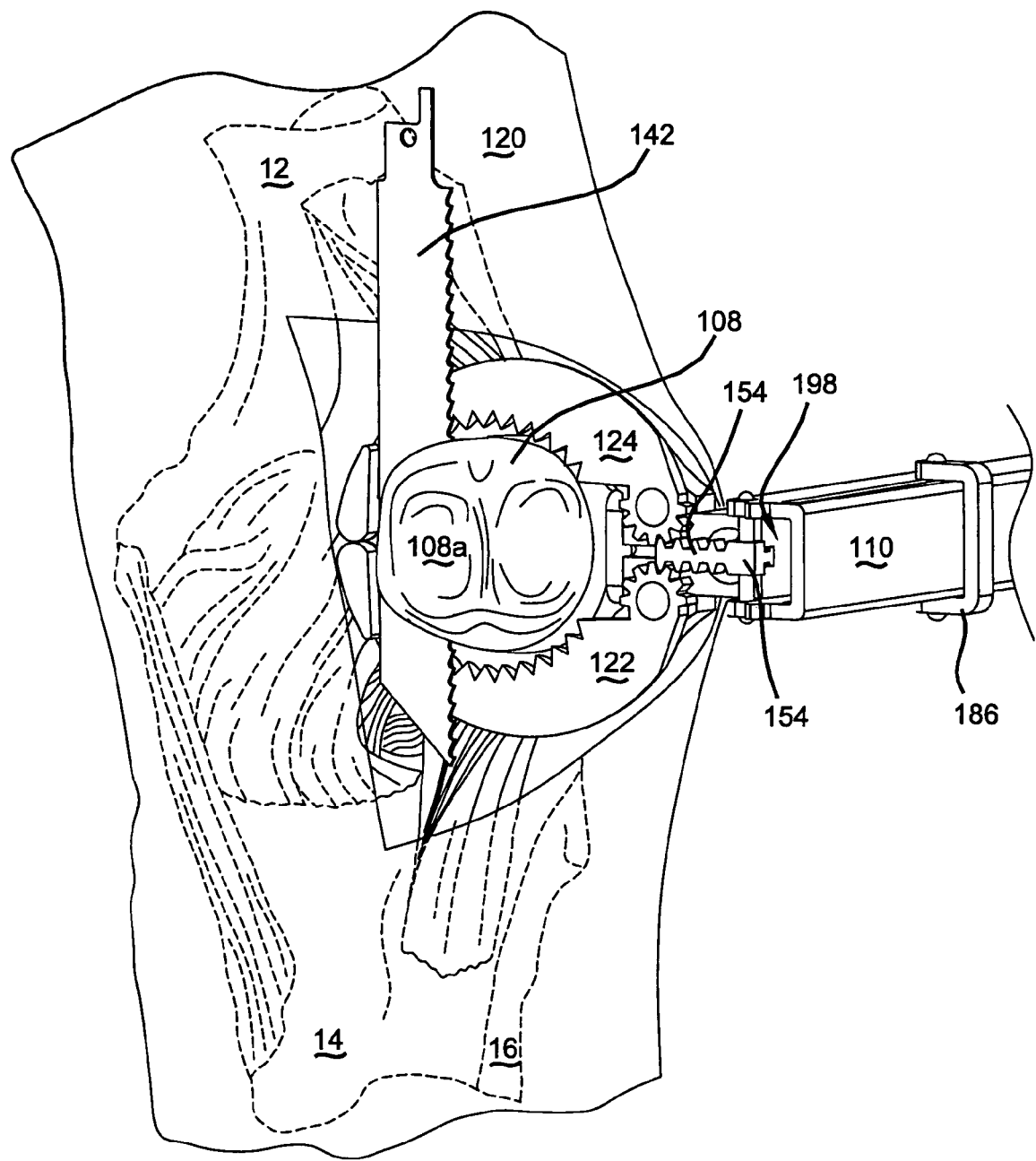
FIG. 11 is similar to FIG. 10 but shows the medical device turning the patella ninety degrees from its normal position.

With reference to FIG. 9 through FIG. 11, the medical device 100 can be used in a minimally invasive procedure. Should a medical professional decide to perform the minimally invasive procedure, the medical professional can make an incision 228 to gain access to the patella 108 having a length of about 2 inches to about 8 inches (about 50 millimeters to about 200 millimeters). Moreover, access to the knee joint 10 can either be on a medial side 230 of the knee or on a lateral side 232. On a medial approach procedure, the incision 228 can be made on the medial side 230 of the knee joint 10 that can have a length as determined by the medical professional such as about 2 inches to about 8 inches (about 50 millimeters to about 200 millimeters). The posterior member 114 of the clamping assembly 104 is passed into the incision 228 in the closed position 214. In the closed position 214, the tips 158 of the jaws 126 may be touching or there may be a space therebetween. Nevertheless, the jaws 126 are in the closed position 214 and urged behind a posterior side 108a of the patella 108 such that the jaws 126 come up beneath the posterior side 108a.

The actuating assembly 102 can then be moved to open the jaws 126 around the patella 108. The jaws 126 can be moved closer to the patella 108 such that the patella 108 sits in proper relation to the saw slot 140 or the reference portion 138 formed on the jaws 126. Once the patella 108 is properly seated, the lever member 110 is pivoted to the clamped position 194 to close the jaws 126 thus engaging the teeth 136 of the jaws 126 into the patella 108. With the patella 108 held by the jaws 126, the plunger member 112 can be pushed towards the clamp end 110a of the handle member 106 thus driving the anterior portion of the clamping assembly towards the exterior surface 118 of the skin 120 just anterior to the patella 108. The anterior member 116 of the clamping assembly 104 makes contact with the exterior surface 118 of the skin 120 just above the patella 108. The patella 108 can be placed in a herniated condition 234 within the clamping assembly 104 and positioned for a resection procedure.

Figure 1:
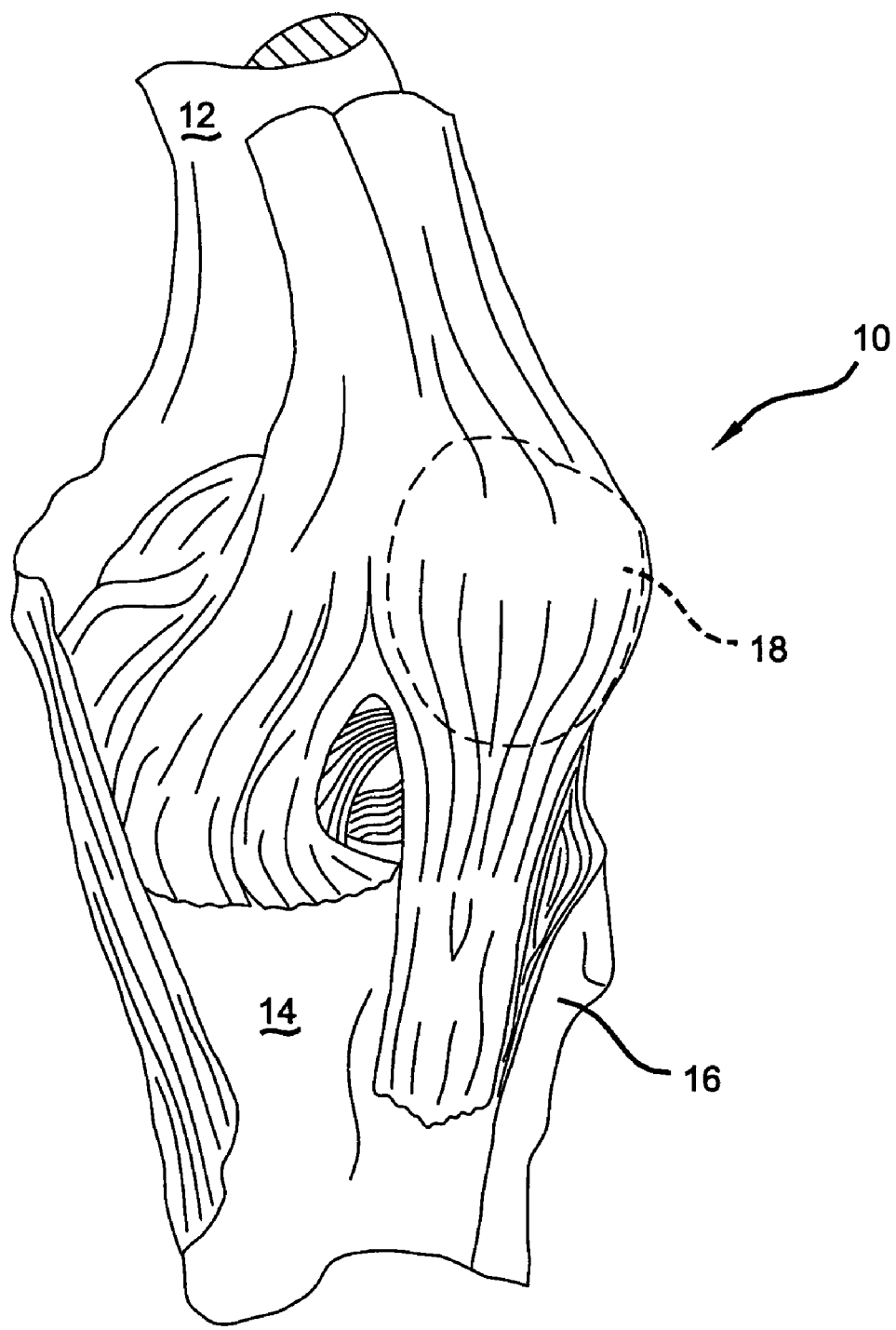
FIG. 1 is a partial front view of a knee joint showing the respective bones, muscle tissue and connective tissue of the knee joint.
Figure 2:
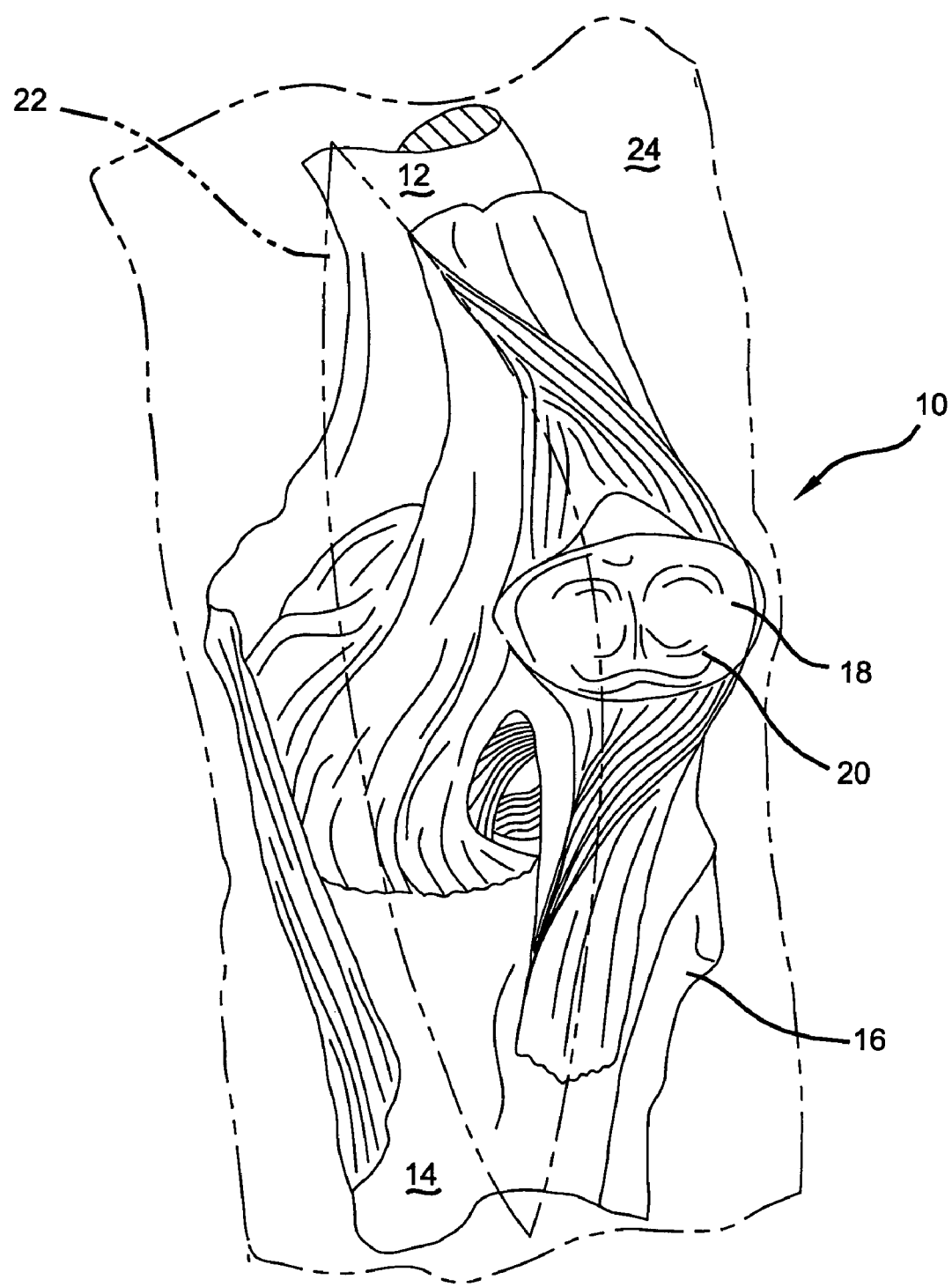
FIG. 2 shows the muscles and the associated connective tissue pulled away from the normal patella position to expose a posterior surface of the patella.
Figure 3:
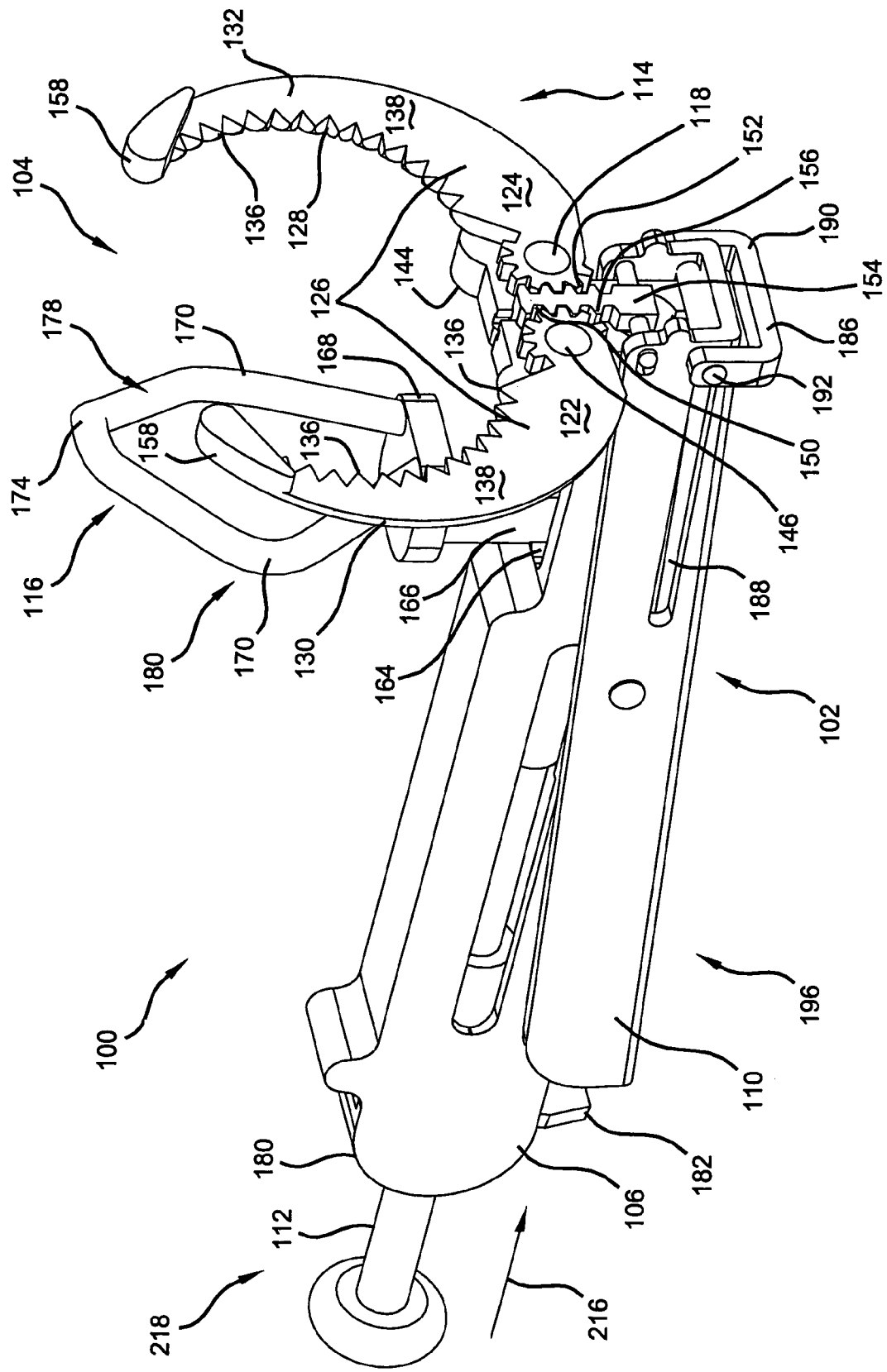
FIG. 3 is a perspective view of a medical device constructed in accordance with the teachings of the present invention showing a clamping assembly and an actuating assembly in an open position.

The patella 108, once secured in the clamping assembly 104, can be everted ninety (90) degrees from its natural rest position (FIG. 1) in the knee joint 10. Once the patella is turned ninety degrees, access to the posterior side 108a of the patella 108 is possible. At this point, the resection tool 142 or other suitable tool can be inserted into the saw cutting slots 140 on either the first jaw 122 or second jaw 124. The resection tool 142 can also be used and indexed off the reference portion 138 on either the first jaw 122 or second jaw 124. It is appreciated that the medical device 100 can be used as a clamp and/or a positioning tool during various resection procedures. It will be further appreciated that the orthogonal orientation of the handle member 106 and the lever member 110 with respect to the clamping assembly may provide improved device geometry. For example, the handle member 106 and the actuating assembly 102 are directed away from the incision 228 thus providing, among other things, more room to work within an area around the incision 228. Moreover, the lever member 110 can be moved to the clamped position 194 by moving the locking slide 186 to the locked position 204 such that one-handed positioning of the clamp is possible.

In the various embodiments of the present invention, the posterior member 114 of the clamping assembly 104 includes the ring assembly 222. To choose correctly among the many individual sizes of the rings 224, the user may measure the patella 108 to insure proper sizing. With proper sizing of the patella 108, the correct ring can be selected from many sized rings (FIG. 8) and attached to the handle member 106. After attaching the properly sized ring to the handle member 106, the ring can be passed into the minimally invasive incision 228 and placed behind the posterior side 108a of the patella 108. It is appreciated that with the ring member 222 no closing of the jaws 126 or other such actuation is applicable. With the ring 220 properly situated behind the posterior surface 108a of the patella 108, the anterior member 116 of the clamping assembly 104 can be urged toward the exterior surface 118 of the skin 120 just anterior to the patella 108 thus moving the patella 108 into the herniated condition 406.

It is appreciated that additional saw guides may be included on the jaws or other suitable locations on the medical device to further facilitate resection of the patella or other bones possibly clamped between the jaws of the medical device. It is also appreciated that the incision 228 can be a medial parapatellar incision. The medical professional can determine that the incision can have a length equal to a range of about two inches (about 50 millimeters) to about eight inches (about 200 millimeters) and can have a length equal to about three inches (about 75 millimeters). It is further appreciated that in a minimally invasive procedure, the length of the incision can be minimized at the discretion of the medical professional, and, as such, the length of the incision may very depending on the patient and suitable medical practices.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A medical device for holding a patella comprising:
a clamping assembly configured to hold the patella, the clamping assembly including an anterior member and a posterior member, the posterior member having first and second jaws movable relative to one another, the top surface of each of the first and second jaws defining and being contained in a jaw plane;
an actuating assembly connected to said clamping assembly each of the first and second jaws separately movable by the actuating assembly, the actuating assembly including a plunger member, the plunger member operable for moving the anterior member relative to the posterior member, the plunger member having a longitudinal axis the longitudinal axis of the plunger member being orthogonally oriented to the jaw plane wherein the plunger member moves the anterior member between an open position and a closed position, the anterior member in the closed position being closer to the pair of jaws relative to the open position.

2. The medical device of claim 1, wherein the clamping assembly includes a pivotable lever coupled to the first and second jaws, the lever moving the first and second jaws between an open position, a closed position and a plurality of positions therebetween.

3. The medical device of claim 2, wherein the first jaw moves at a first rate and the second jaw moves at a second rate, the first rate equal to the second rate.

4. The medical device of claim 2, wherein the first jaw moves at a first rate and the second jaw moves at a second rate, the first rate not equal to the second rate.

5. The medical device of claim 2, further comprising a lock member, the lock member operable for preventing rotation of the lever and holding the first and second jaws in the closed position.

6. The medical device of claim 5, the lock member operable for holding the first and second jaws in a plurality of positions between the closed position and the open position.

7. The medical device of claim 1, wherein the anterior member includes two arcuate rod portions forming a concave surface, the concave surface disposed toward the first and second jaws and configured to contact skin above the patella and to hold the patella against the posterior member.

8. The medical device of claim 1 further comprising a handle member connected to the clamping assembly and the actuating assembly, the anterior member disposed within a groove in the handle member, the handle member including a locking tab operable for locking the anterior member relative to the posterior member.

9. The medical device of claim 1, wherein each of the first and second of jaws includes a reference portion, the reference portion configured such that a cutting tool can abut the reference portion.

10. The medical device of claim 1, wherein each of the first and second of jaws includes a cutting slot, the cutting slot configured to hold a cutting tool.

11. The medical device of claim 1, wherein the posterior member and the anterior member are operable to hold the patella about ninety degrees from the patella's normal position.

12. A medical device for holding a patella comprising:
a clamping assembly including a pair of jaws and an anterior member, the pair of jaws the top surface of each of the jaws defining and being contained in a jaw plane and configured to engage the patella, the anterior member movable relative to the pair of jaws and configured to contact skin above the patella and urge the patella toward the pair of jaws, the anterior member forming a concave surface disposed toward the pair of jaws;
a handle member including a plunger member connected to the anterior member, the handle member having a longitudinal axis orthogonally oriented to the jaw plane, the plunger member operable for moving the anterior member between an open position and a closed position, the anterior member in the closed position closer to the pair of jaws relative to the open position; and
an actuating assembly connected to the clamping assembly and the handle member, the actuating assembly including a lever member that pivots about the handle member, the lever member connected to the pair of jaws and moving the pair of jaws between an open position and a closed position, the pair of jaws in the closed position configured to engage the patella.

13. A medical device for holding a patella comprising:
a clamping assembly including a posterior member comprising a pair of jaws and an anterior member, the pair of jaws configured to engage the patella, the anterior member configured to contact skin above the patella and urge the patella toward the pair of jaws, wherein the anterior member includes two arcuate rod portions forming a concave surface, the concave surface disposed toward the pair of jaws;

a handle member including a plunger member connected to the anterior member and moving the anterior member between an open position and a closed position, the anterior member in the closed position closer to the pair of jaws relative to the open position; and an actuating assembly connected to the clamping assembly and the handle member, the actuating assembly including a lever member that pivots about the handle member, the lever member connected to the pair of jaws the lever member configured to separately move each of the jaws between an open position and a closed position, the pair of jaws in the closed position configured to engage the patella.

14. The medical device of claim 13, wherein the plunger member is disposed within the handle member.

15. The medical device of claim 13, further comprising a slide member connected to the lever member, the slide member operable to hold the pair of jaws in the closed position.

16. The medical device of claim 15, wherein the slide member operable to hold the pair of jaws in a plurality of positions between the closed position and the open position.

17. The medical device of claim 13 further comprising a locking tab that is connected to the handle member, the locking tab operable to hold the anterior member in the open position, the closed position and a plurality of positions therebetween.

18. The medical device of claim 13, wherein each of the jaws includes a reference portion, the reference portion configured such that a cutting tool can abut the reference portion.

19. The medical device of claim 13, wherein each of the jaws includes a cutting slot, the cutting slot configured to hold a cutting tool.

20. The medical device of claim 13, wherein the posterior member and the anterior member are operable to hold the patella about ninety degrees from the patella normal position.

* * * * *